(12) United States Patent
Brown et al.

(10) Patent No.: US 6,983,748 B2
(45) Date of Patent: Jan. 10, 2006

(54) DRY POWDER INHALER

(75) Inventors: David Brown, Helsinki (FI); Esko Kauppinen, Helsinki (FI); Juha Kurkela, Espoo (FI); Wiwik Watanabe, Sunnyvale, CA (US); Jorma Jokiniemi, Vantaa (FI); Esa Muttonen, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/399,913

(22) PCT Filed: Oct. 26, 2001

(86) PCT No.: PCT/FI01/00924

§ 371 (c)(1),
(2), (4) Date: Oct. 1, 2003

(87) PCT Pub. No.: WO02/34320

PCT Pub. Date: May 2, 2002

(65) Prior Publication Data

US 2004/0069303 A1 Apr. 15, 2004

(30) Foreign Application Priority Data

Oct. 27, 2000 (FI) .................................. 20002363

(51) Int. Cl.
*A61M 15/00* (2006.01)
(52) U.S. Cl. .............................. 128/203.15; 128/203.19
(58) Field of Classification Search ........... 128/200.11, 128/200.18, 200.21, 200.23, 203.12, 203.15, 128/203.19, 203.21
See application file for complete search history.

(56) References Cited

U.S. PATENT DOCUMENTS

| 3,831,606 A | 8/1974 | Damani |
| 3,948,264 A | 4/1976 | Wilke et al. |
| 4,200,099 A | 4/1980 | Guenzel et al. |
| 4,240,418 A | 12/1980 | Rosskamp et al. |
| 4,524,769 A | 6/1985 | Wetterlin |
| 5,113,855 A | 5/1992 | Newhouse |
| 5,161,524 A | 11/1992 | Evans |
| 5,301,666 A | 4/1994 | Lerk et al. |

(Continued)

FOREIGN PATENT DOCUMENTS

GB 2165159 A 4/1986

(Continued)

OTHER PUBLICATIONS

Derwent Abstract of WO 93/03782.

(Continued)

*Primary Examiner*—Teena Mitchell
(74) *Attorney, Agent, or Firm*—Finnegan, Henderson, Farabow, Garrett & Dunner, LLP

(57) ABSTRACT

A device for delivering a powdered medicament by inhalation comprises an air inlet passage having low pressure-drop and low turbulence for stabilizing air flow before aerosolization, a dosing cup in the region of reduced air velocity to delay aerosolization, a high pressure drop throat to generate a high velocity flow, a rapidly expanding diverging passage to create a free jet of air with high turbulence and an outlet passage having large cross-sectional area to control the rate of dissipation of the free jet. The device is simple yet capable of consistently providing uniform and effective powder aerosolization and deagglomeration over a variety of patient inhalation profiles.

30 Claims, 11 Drawing Sheets

U.S. PATENT DOCUMENTS

| | | | |
|---|---|---|---|
| 5,327,883 A | | 7/1994 | Williams et al. |
| 5,349,947 A | | 9/1994 | Newhouse et al. |
| 5,388,572 A | | 2/1995 | Malhauser et al. |
| 5,575,280 A | * | 11/1996 | Gupte et al. ............ 128/203.15 |
| 5,676,130 A | * | 10/1997 | Gupte et al. ............ 128/203.19 |
| 5,724,959 A | | 3/1998 | McAughey et al. |
| 5,727,546 A | | 3/1998 | Clarke et al. |
| 5,875,776 A | | 3/1999 | Vaghefi |
| 6,026,809 A | * | 2/2000 | Abrams et al. ......... 128/203.15 |
| 6,065,472 A | * | 5/2000 | Anderson et al. ....... 128/203.21 |
| 6,119,688 A | * | 9/2000 | Whaley et al. ......... 128/203.15 |
| 6,182,655 B1 | | 2/2001 | Keller et al. |
| 6,332,461 B1 | * | 12/2001 | Hyppola ................. 128/203.15 |
| 6,371,111 B1 | * | 4/2002 | Ohki et al. ............. 128/203.15 |
| 6,655,381 B2 | * | 12/2003 | Keane et al. ........... 128/203.15 |
| 6,810,874 B1 | * | 11/2004 | Koskela et al. ......... 128/203.15 |

FOREIGN PATENT DOCUMENTS

| | | |
|---|---|---|
| WO | WO 92/00771 | 1/1992 |
| WO | WO 92/09322 | 6/1992 |
| WO | WO 93/03782 | 3/1993 |
| WO | WO 97/20589 | 6/1997 |
| WO | WO 97/26934 | 7/1997 |
| WO | WO 98/26828 | 6/1998 |
| WO | WO 99/07426 | 2/1999 |

OTHER PUBLICATIONS

Derwent Abstract of WO 97/20589.

* cited by examiner

DRY POWDER INHALER

This application is a U.S. national stage filing of PCT International Application No. PCT/FI01/00924, filed on Oct. 26, 2001. This application also claims the benefit of priority under 35 U.S.C. § 119(a) to Finnish patent application no. 20002363, filed on Oct. 27, 2000.

FIELD OF THE INVENTION

The present invention relates to a device for dispensing of powdered material by inhalation. In particular, it relates to an inhaler device for aerosolizing a dose of powdered medicament for pulmonary delivery by inhalation.

BACKGROUND OF THE INVENTION

Inhalation has become the primary route of administration in the treatment of asthma. This is because, in addition to providing direct access to the lungs, medication delivered through the respiratory tract provides rapid and predictable onset of action and requires lower dosages compared to the oral route.

Pressurised metered dose inhalers (pMDIs) are currently the most commonly used inhalation devices. Such devices comprise a canister containing a suspension of fine drug particles in a propellant gas. Upon actuation, the aerosol contents are expelled, through a metering valve, and a metered dose is propelled into the lungs of the patient. The biggest threat to the continued use of pMDIs is that they rely on propellants, namely chlorofluorocarbons (CFCs), which have been implicated in the depletion of the ozone layer.

Several types of dry powder inhalers (DPIs) have been developed, in which the inhalation air of the patient is used for dispersing the drug particles. DPIs are user friendly, as they do not require coordination between actuation and inspiration. The powdered medicament is arranged as unit dose containers. e.g. blister packs, cartridges or peelable strips, which are opened in an opening station of the device. Alternatively, the unit dose is measured from a powder reservoir by means of a metering member, e.g. a dosing cup.

To increase flowability and dosing accuracy of the powdered medicament, the fine drug particles of respirable size are typically mixed with coarser carrier particles to form an ordered mixture, wherein line drug particles are attached to the larger carrier particles. This technique complicates the powder aerosolization process and, in particular, necessitates the break-up of the drug/carrier agglomerates before they enter the patient's mouth and throat, where individual large particles and agglomerated large and small particles tend to deposit. Effective aerosolization and deagglomeration of the powder requires that forces exerted on particles (be they on exposed surfaces of the device, between drug and carrier particles or between drug and drug particles) must be overcome under all expected inhalation profiles.

The aim of the inhaler devices is to produce a high Fine Particle Dose (FPD) of particles in the respirable size range. However, the ability of a device to aerosolize and deagglomerate the drug particles into a respirable particle size range depends on the patient's inspiration technique for most DPIs currently available. An ideal dry powder inhaler would provide uniform powder aerosolization and deagglomeration over a wide range of inhalation profiles, so as to generate consistent doses of respirable particles in the final dispersion.

Various techniques have been used in DPIs to aerosolize and deagglomerate drug powder during inhalation. These include turbines and impellers (e.g. U.S. Pat. Nos. 4,524,769, 3,831,606 and 5,327,883) or other mechanical means (WO 98/26828), compressed gas (e.g. U.S. Pat. No. 5,113,855, 5,349,947 and 5,875,776), cyclones (e.g. U.S. Pat. No. 5,301,666 and WO 99/07426), electrostatic suspension and piezoelectric vibration (e.g. U.S. Pat. No. 3,948,264 and WO 97/26934), venturis (U.S. Pat. Nos. 4,200,099, 4,240,418 and WO 92/00771) and impactors (U.S. Pat. No. 5,724,959). Several patents have used electronic or other means of sensing of the airflow or pressure drop through the device to trigger the release of drug particles into the airstream so as to coordinate activation of release and inhalation (e.g. WO 93/03782, WO 97/20589 and U.S. Pat. No. 5,388,572) or a means to mechanically control the patient's inspiration rate (U.S. Pat. Nos. 5,727,546 and 5,161,524). In general, these DPIs have become more complicated and expensive.

Flow behavior in a DPI is critical for the aerosolization and particle break-up processes, especially if the device is passive. i.e. has no mechanical or electrical augmentation or triggering mechanisms. In order to maximize the Fine Particle Fraction (FPF) and provide a consistent dose over a wide range of patient inhalation profiles, particular attention should be paid to the levels of turbulence in critical regions where drug-carrier break-up is likely to occur. Therefore, we have performed Computational Fluid Dynamics (CFD calculations on various inhalers to characterize the steady-state flow behaviour of the devices. In a number of dry powder inhalers, inlet air is focused on the dosing cup or holding portion of the metered dose (e.g. WO 99/07426, WO 92/00771 and WO 92/09322) and thus the vast majority of the powder is aerosolized at the very beginning of the inhalation cycle. Typically, the designers of inhalers place importance on immediate aerosolization of powder under the belief that deep lung deposition relies on introduction of aerosol very early in the inhalation cycle. However, tests have concluded that initial aerosolization is typically not a serious issue. Deep lung deposition to targeted sites depends much more strongly on delivering particle doses in the correct size range. Too large particles tend to impact on surfaces in the upper airways due to their high inertia and too small particles tend to reach surfaces due to Brownian diffusion. In fact, even if most of the powder is aerosolized immediately and effectively it tends to be at very low flow velocity conditions and thus low turbulence levels. Thus, when the particles exit the device, there is little turbulent shear energy available for particle deagglomeration and a significant fraction of the dose is thus deposited in the upper airways since they are often still attached to larger carrier particles or exist as large agglomerates.

Based on CFD calculations, a number of deficiencies in known passive inhalers have been identified. These include:

Poor control of flow. Peak velocities, in general, occur slightly downstream of inlets and the jet is focused in the vicinity of the dosing cup. The majority of the pressure drop and highest levels of turbulence occur upstream of the dosing cup, before particles are aerosolized. This is essentially wasted energy that could be used more efficiently downstream of particle dispersion in order to effectively break-up drug/carrier particles. In addition, there are typically significant "dead" zones in and around the dosing cup, which reduces particle aerosolization and thus increases the energy required to disperse particles. Large recirculation zones downstream of the dosing mechanism provide potential sites for particle redeposition.

Uncontrolled turbulence. In current DPIs, turbulence in the outlet free jet is uncontrolled and will be substantially affected by the patient's inhalation technique and mouth geometry. Ultimately, this can lead to significant variation in fine particle fraction from patient to patient even using the same device under identical flow conditions.

Inappropriate release time. Experimental data shows that in present DPIs aerosolization of particles occurs at the initiation of the inhalation cycle, long before the flow is developed and velocities and turbulence reach peak values. To maximize break-up of particles due to turbulence, it is desirable to aerosolize the powder later in the inhalation cycle where turbulence is higher and the flow more developed. This has the additional benefit that powder that is aerosolized in a steady state flow condition is less likely to be redeposited in recirculation zones.

Current passive devices operate in a range where a change in the flow rate or pressure drop across the device (which translates into a change in the turbulence experienced by the aerosols) leads to very significant changes in the aerosol distribution in the patient's lungs. It is more desirable to operate in a range where the aerosol properties are not strongly influenced by the inhalation rate. This, again, implies that aerosolization should occur near maximum turbulence conditions for a low flow rate (pressure drop) peak, such as would occur in an elderly or adolescent patient. Higher flow rates, as would occur in a healthy adult, should not significantly alter the resulting aerosol properties. Thus, sufficient turbulence should be achieved to break-up drug and carrier particles already at low flow rate conditions.

SUMMARY OF THE INVENTION

The object of the present invention is to construct a dry powder inhaler, which is simple but capable of providing uniform and effective powder aerosolization and deagglomeration over a wide range of patient inhalation profiles, so as to generate consistent doses of respirable particles. Unlike prior dry powder inhalers, the device uses detailed consideration of specific fluid dynamics to produce shear forces in specific regions of the flow and at optimal times in the inhalation flow profile.

An important aspect of the device is the passive control of the shear forces exerted on and between dosage particles, both during the powder aerosolization process and during the deagglomeration process once the powder is effectively acrosolized. Key to controlling these shear forces is the ability to control the carrier gas velocities and turbulence levels throughout the device. The device of the invention avoids the need for complicated mechanical, electrical or other means of deagglomerating particles and/or coordinating inhalation and dose delivery. Thus the device is simple to produce, consistent in operation and is not susceptible to mechanical failure.

The inhaler of the invention is called a delayed action aerosolization and deagglomeration device. It releases particles into the main stream later in the inhalation cycle where flow rates are higher and turbulence more developed. The high velocity air, which is used in the device to aerosolize and deagglomerate the powder, is achieved by inspiratory effort alone. Furthermore, by utilizing a well located constriction in the flow, high velocities and especially high levels of turbulence can be achieved already at low inspiration rates. The highest pressure drop and most intense turbulence occurs downstream of the aerosolization zone in a controlled region largely unaffected by the patient's mouth and far from walls such that the turbulence damping and re-deposition is reduced. Further, due to the low velocity of drug particles as they exit the inhalation device, relatively low amounts of drug will be deposited in the upper airways of the user. Compared to conventional DPIs, the device of the invention provides better control of the deagglomerating shear forces, and thus the particle size distribution and the Fine Particle Dose (FPD). Furthermore, the FPD can be ensured as it only depends on a minimum inhalation rate and not on any coordinated action of the patient or complex activation or release mechanism. The dosage that is withdrawn is more consistent and less dependant on inspiratory flow profiles than in prior devices.

The device of the invention may be essentially passive. Thus the dose of powdered medicament may be aerosolized and deagglomerated essentially by the action of the air stream that is achieved by inhaling through the device without additional mechanical, electrical or other triggering or augmenting means for aerosolizing or deagglomerating particles. Most preferably, no other means than the aerodynamics of the air inhaled through the device participates to the aerosolization and deagglomeration of the dose of powdered medicament.

Accordingly the present invention provides a device for dispensing powdered medicament by inhalation, comprising an air inlet passage, a transition passage connected to the air inlet passage, said transition passage comprising a holding portion for a dose of powdered medicament and means for creating a region of reduced air velocity, a converging passage connected to the transition passage the end of the converging passage forming a throat, a diverging section connected to the throat, and an air outlet passage connected to the diverging section, and wherein the cross-sectional area of the throat is smaller than the minimum cross-sectional area of the air inlet passage, the transition passage and the outlet passage, the dose of powdered medicament being aerosolized from the holding portion by means of air stream produced by inhalation.

The air inlet passage is dimensioned such that it provides low pressure drop and low turbulence. Preferably the flow Reynolds Number of the air inlet passage is below 5000, more preferably below 4000, and the cross-sectional area essentially constant. The length of the air inlet passage is preferably greater than three times its shortest dimension.

The transition passage comprises means for creating a region of reduced air velocity as well as the holding portion for a dose of powdered medicament. Said holding portion is disposed in the transition passage preferably in the region of reduced air velocity. Reduced air velocity delays aerosolization and/or reduces the rate of aerosolization from the dosing cup until the flow is sufficiently developed. Thus, the turbulent shear forces are near their maximum levels downstream resulting in effective deagglomeration.

The region of reduced air velocity in the transition passage is created preferably by means of one or several turns, an expansion or combination thereof. The air inlet passage is preferably smoothly integrated with the transition passage. The transition passage is preferably smoothly integrated with the converging passage.

The shape of the holding portion for a dose of powdered medicament is preferably such that it is smoothly integrated into the wall of the transition passage. Such holding portion is e.g. a dosing cup of a metering member adapted to meter a dose of powdered medicament from a medicament reservoir of the device.

The cross-sectional area of the throat is preferably less than 50%, more preferably less than 35%, of the minimum cross-sectional area of the air inlet passage, the transition passage and the outlet passage The cross-sectional area of the outlet passage is preferably larger than the cross-sectional area of the air inlet passage, and preferably larger than three times the cross-sectional area of the throat. The device may additionally comprise an impactor plate positioned in the outlet passage.

The device of the invention is preferably a multi-dose dry powder inhaler of a reservoir type. However, the principle of the invention may be used as well for other types of dry powder inhalers, e.g. inhalers where the powdered medicament is arranged as unit dose containers such as blister packs, cartridges or peelable strips.

DETAILED DESCRIPTION OF THE INVENTION

Figure 1:
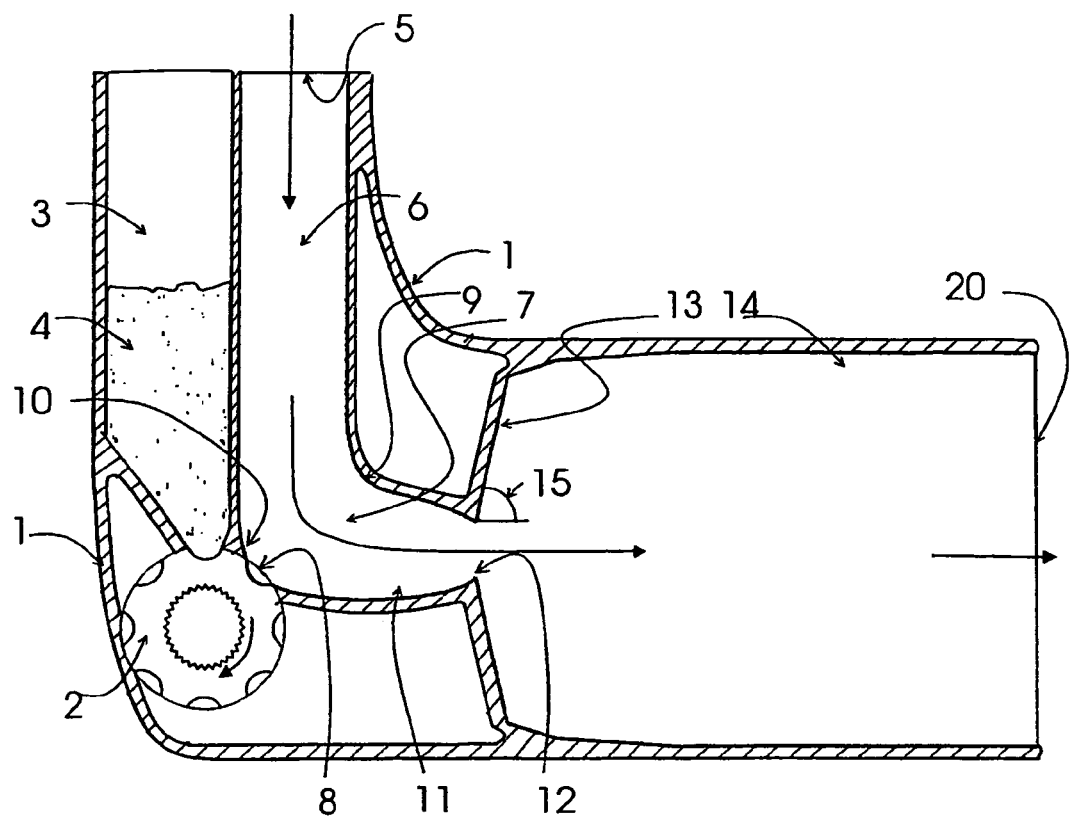
FIG. 1 shows a cross section of one embodiment of the device according to the invention along a vertical symmetry plane.

The invention relates to a device for dispensing powdered medicament by inhalation comprising an air inlet passage, a transition passage connected to the air inlet passage, said transition passage comprising a holding portion for a dose of powdered medicament and means for creating a region of reduced air velocity, a converging passage connected to the transition passage the end of the converging passage forming a throat, a diverging section connected to the throat, and an air outlet passage connected to the diverging section, and wherein the cross-sectional area of the throat is smaller than the minimum cross-sectional area of the air inlet passage, the transition passage and the outlet passage, the dose of powdered medicament being aerosolized from the holding portion by means of air stream produced by inhalation.

The air inlet passage should provide low pressure drop and low turbulence. The air inlet passage is dimensioned so that, at the maximum flow rate expected in the device, the flow at the end of the inlet passage is, at most, at a low turbulence level. Based on the minimum inlet passage dimension, the cross section of the air inlet passage is defined such that the Reynolds Number (Re) for the flow at peak flow conditions is below 5000, preferably below 4000. Here, the Reynolds Number for the inlet passage (6) is defined as $$Re = \frac{\rho V L}{\mu}$$

where $\rho$ and $\mu$ are the density and viscosity of air at ambient conditions. I' is the average velocity of the gas in the inlet passage and L is the minimum dimension of the inlet passage. The inlet passage has preferably essentially constant cross-section and preferably essentially rectangular shape so as to moderate the turbulence level before the flow reaches the holding portion of the powder. The air inlet passage is preferably straight, and the length of the air inlet passage is preferably greater than three times the shortest dimension of the air inlet passage.

The air inlet passage is followed by the transition passage having means for creating a region of reduced air velocity. A holding portion for a dose of powdered medicament is preferably disposed at the region of reduced air velocity. The term "region of reduced air velocity" refers to a region of the passage where the air velocity is essentially less than the air velocity in the surrounding region along the path of air stream.

There are several options how to create a region of reduced air velocity in the transition passage.

In one preferred embodiment of the invention, the transition passage forms a turn, the transition passage thus being in the form of a turning passage. The turn creates a region of reduced air velocity close to the outer wall of the turn. The turning angle (the angle between the axis of the air inlet passage and the axis of the converging passage) is typically between 10 and 170 degrees, preferably between 45 and 135 degrees, more preferably between 70 and 110 degrees, most preferably approximately 90 degrees. In the preferred embodiment, the radius of curvature of the inner wall of the turning passage is dimensioned such that the turning angle is larger than a critical value so that the flow remains attached (without recirculation) on the inside of the turn during the inhalation process. Calculations have indicated that in order to eliminate recirculation in the region of the inner wall, the radius of curvature of the inner wall of the turning passage should be greater than 20%, preferably about one half, of the shortest dimension of the cross-section of the air inlet passage. The cross-section of the turning passage can be of any shape, but preferably it is essentially rectangular.

The turning passage, as defined above, includes on its outer face one or more holding portions. e.g. dosing cups, for a dose of powdered medicament. The dosing cup is preferably smoothly integrated into the outer face of the turning passage so as to reduce small-scale recirculation in the cup. The cross-section of the dosing cup can be of arbitrary shape provided that it is smoothly integrated into the outer wall of the turning passage. The cross-section of the dosing cup is most suitably semicircular. The angles between the dosing cup wall and the outer wall of the turning passage should be less than 90 degrees, preferably 45 degrees or below. The dosing cup thus becomes an integral part of the aerosolization and release mechanism. The cross-sectional area of the turning passage may be equal or preferably greater than the cross-sectional area of the inlet passage. In the preferred embodiment, the combination of rapid turning, and the increase of the cross-sectional area, e.g. due to the dosing cup, causes a well defined recirculation region to develop at the outside wall of the turning passage. This has the effect of reducing the velocity of fluid in the dosing cup so as to delay aerosolization and/or reduce the rate of aerosolization from the dosing cup until the flow is sufficiently developed and the turbulent shear forces are near their maximum levels downstream. The inlet passage and the turning passage are preferably continuous, and it is preferred that the air inlet passage is smoothly integrated with the turning passage.

In another preferred embodiment of the invention, the transition passage comprises an expansion region. In this case, the transition passage does not need to comprise a turn. Here, reduced velocity in the region of the dosing cup is created by increasing cross-sectional area of the transition passage. The cross-sectional area of the expansion is preferably from 1.25 to 10, more preferably from 2 to 5, times larger than that of air inlet passage. The expansion is preferably rapid, such that a well-defined region of reduced air velocity region is formed near the wall of the expansion. The opening angle of the expansion is preferably between 10 and 135 degrees, suitably between 20 and 90 degrees. The dosing cup is preferably situated immediately downstream of the expansion so as to reside in the reduced velocity region. The cross-sectional shape of the expansion is preferably essentially rectangular.

In still another preferred embodiment of the invention, the transition passage comprises a multiple turning region. In this case, reduced velocity in the region of the dosing cup is created by multiple turns in the flow even though the cross-section of the transition passage is essentially constant. For example, a multiple turn consist of two turns in succession. The distance between the turns is preferably from 0.5 to 2, suitably about 1, times the diameter of the transition passage. The turning angle of each turn is preferably between 10 and 135 degrees, suitably between 20 and 90 degrees. The cross-sectional shape of the multiple turn is preferably essentially rectangular. The dosing cup is preferably situated immediately downstream of the multiple turn so as to reside in the reduced velocity region.

The converging passage is preferably smoothly connected to, and integrated with, the transition passage. The cross-section can be of arbitrary shape, but is preferably rectangular. The converging section should be long enough to allow the flow at the outer wall of the transition passage to fully reattach so that the flow is predominantly in the downstream direction before entering the throat formed at the end of the converging passage distal to the transition passage. The rate of constriction should be less than that which would cause any additional recirculation regions upstream of the throat. The throat is smoothly connected to the converging passage, and can be of arbitrary shape, but is preferably oval. The oval shape is preferred because it increases the zone of interaction of the high velocity gas exiting the throat with the low velocity gas in the diverging section. This has the effect of increasing the dispersion rate and thus more rapidly reduces the strength of the issuing jet. This is beneficial in terms of reducing particle deposition in the patients' mouth and throat due to inertial impaction. The cross sectional area of the throat is specified based on the pressure drop requirements for the device. Higher pressure-drop requirements entail smaller throat areas. So long as the throat cross sectional area is substantially smaller than the minimum cross sectional area of the inlet, turning, converging and outlet passages, the pressure drop across the entire device is effectively controlled by the throat. The cross-sectional area of the throat is preferably less than 50%, more preferably less than 35%, of the minimum cross-sectional area of the air inlet passage, the turning passage and the outlet passage. The range of peak pressure drops across the device is suitably from 0.5 to 20 kPa and the range of peak flow rates through the device is typically from 1 to 150 liters per minute. In the preferred embodiment, the required pressure drop for a maximum flow rate of 60 liters per minute is about 6.5 kPa. For other design requirements, the cross-sectional area of the throat can be adjusted considerably so long as it is preferably less than 50% of the minimum cross-sectional areas of the inlet, transition and converging passages.

The throat joins diverging section preferably at a sharp divergence angle. The requirement of the divergence angle is such that the flow issuing from the throat cannot negotiate the rapid turning and becomes separated, thus forming a free jet in the diverging section and outlet passage. In the preferred embodiment, divergence angle is about 87 degrees, though it can vary from about 10 degrees to 180 degrees. The radius of curvature of the throat corner should be small enough such that the now readily detaches from the wall of the diverging section and creates a free jet of air. In the preferred embodiment, this radius of curvature is about 1% of the minimum throat dimension, though it can range between 0 to 100% of the minimum throat dimension. The purpose of the free jet is to create a region of high shear stress and thus generate high levels of turbulence far from the damping effects of the nearby walls. Localized high levels of turbulence immediately downstream of the throat at flow conditions at or near peak (due to the delayed release of particles from dosing cup) result in strong shear forces between agglomerated particles and thus high deagglomeration efficiency for the aerosolized powder.

The outlet passage, which has a relatively large cross-sectional area, is connected to the diverging section. Its cross-sectional area is preferably larger than the cross-sectional area of the air inlet passage, and preferably larger than three times, more preferably larger than twenty times, the cross-sectional area of the throat. The cross-section of the outlet passage is preferably constant. The cross-sectional shape of the outlet passage is preferably oval. The end of the outlet passage forms the mouthpiece of the device. The length of the outlet passage is selected such that a controlled free jet is formed before entering the mouth of the user. Thus, the dependence of the turbulence on the mouth geometry of the user is reduced. In many known inhalers, the jet is focused very close to the tongue, leading to high deposition of particles. In addition, the mouth is, more or less, closed during inhalation. Turbulence is, thus, not maximized due to the proximity of the mouth surfaces which dampen the turbulence. In the present device, the jet is focused further back in the mouth and away from the tongue. In addition, because of the relatively large cross-sectional area of the outlet passage, the mouth is forced to be more open, thus reducing the dampening effects of the mouth surfaces on the turbulence.

To maintain the control of particle release in the case of exhalation into the device due to incorrect use, the device may additionally comprise means to reduce backflow caused by the exhalation. Such means comprise an extension of the diverging section to form a dead end zone the divergence angle being greater than 90 degrees, preferably greater than 120 degrees. The dead end promotes a highly disturbed, high pressure drop flow with large recirculation when the flow direction is reversed. This will significantly reduce the flow through the device, when the user exhales into the device, and prevents the aerosolization of drug and carrier particles.

The device may additionally comprise an impaction plate positioned in the outlet passage. The impaction plate is placed in the path of the free jet, but far enough downstream to allow some particle break-up due to turbulent shear. Large carrier particles and drug-carrier agglomerates that have not been broken up are impacted on the plate to enhance deagglomeration. Already deagglomerated drug particles, with low inertia, pass the plate without impaction. A second benefit of this feature is that the free jet is diminished before entering the mouth.

The device of the invention is further illustrated below by way of examples with reference to FIGS. 1 to 15.

The unique features of the device relate to the geometry of such internal portions of the inhaler, which are in direct contact with the moving air stream. However, for the sake of completeness, a mechanism for filling and positioning the dosing cup are now briefly explained with reference to FIG. 1, even though they are not essential features of the invention.

FIG. 1 shows a cross section of the inhaler according to the invention along the vertical symmetry plane. The device has a body (1) and a medicament reservoir (3) for a certain supply of powdered medicament (4). The reservoir (3) has a rectangular cross-section and a tapering end portion with an orifice at the bottom. A dose of medicament is metered and brought into the air channel of the device by means of a manually rotatable metering drum (2) equipped with a plurality of peripheral dosing cups (8). The metering drum (2) is secured below the reservoir (3) such that in one position of the metering drum (2) a dosing cup (8) is filled with a metered dose of the powdered medicament falling from the medicament reservoir and in another position of the metering drum (2) the filled dosing cup (8) is brought into the air channel of the device. The stepwise one-directional rotation of the metering drum (2) can be achieved for example by means of a depressible cover engaging with tooth of the metering drum (2) analogue to a ratchet mechanism as described in patent publication WO 92/09322. However, also other mechanisms and structures well known in the art for metering and bringing a dose of powdered medicament to the air channel may be used in the device of the invention.

Figure 2:
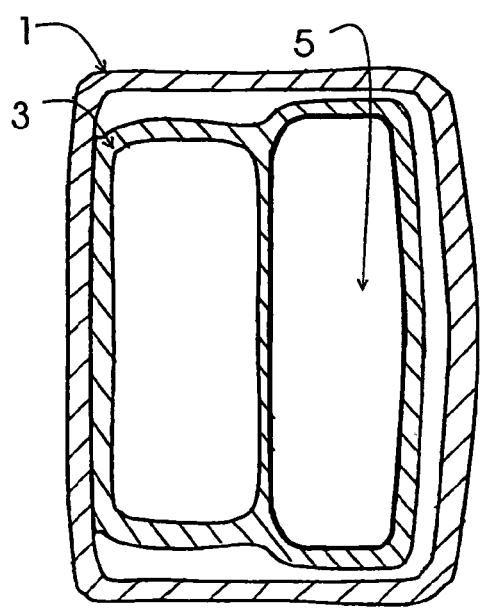
FIG. 2 shows a cross section of the air inlet passage of the device of FIG. 1 along a horizontal plane.
Figure 3:
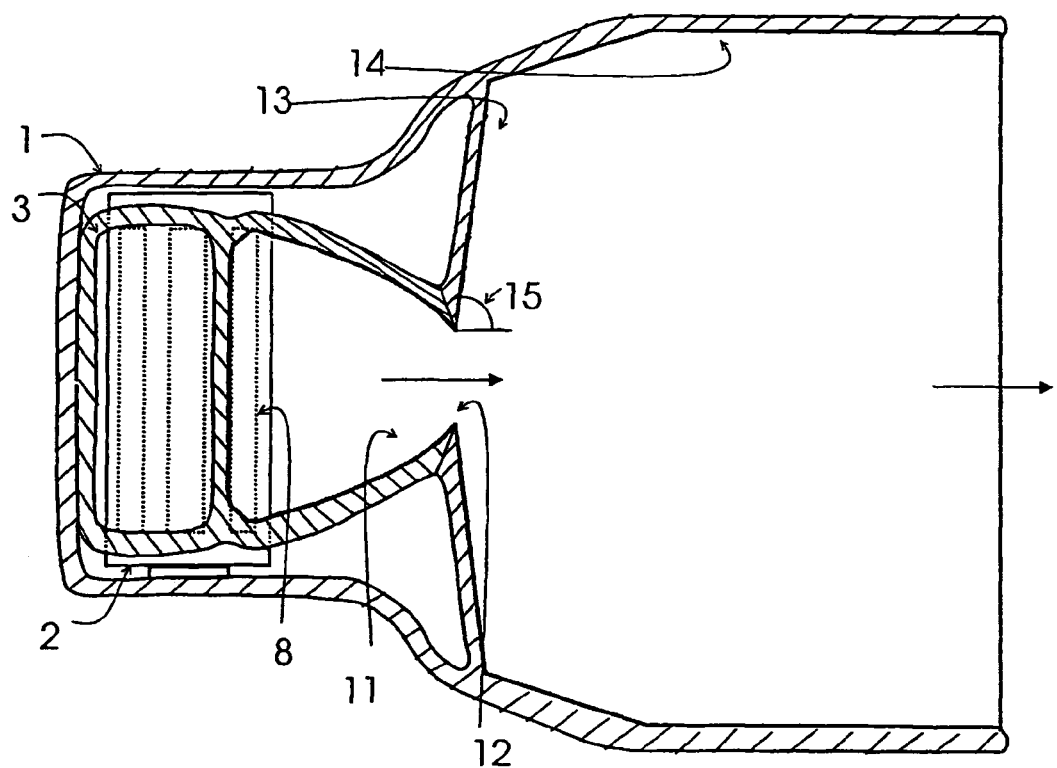
FIG. 3 shows a cross section of the device of FIG. 1 along a horizontal plane at the center of the converging passage.
Figure 4:
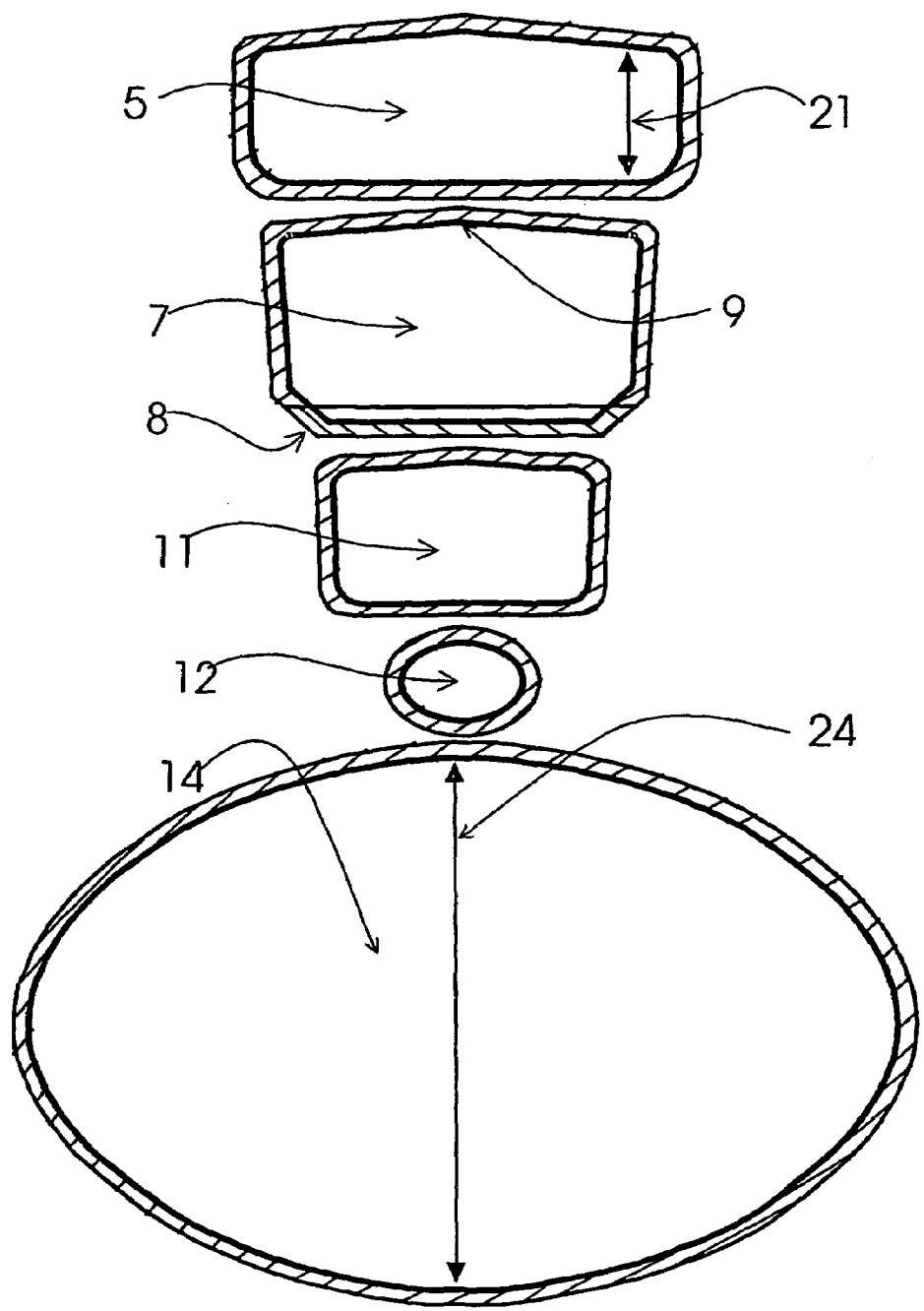
FIG. 4 shows the cross sections of the maximum area of the air inlet passage, transition passage, converging passage, throat, and outlet passage of the device of FIG. 1.

The main parts of the air channel of the device are the air inlet passage (6), a transition passage (7), a converging passage (11) the end of which forms a throat (12), a diverging section (13) and an air outlet passage (14). When a metered dose of powdered medicament has been brought to the air channel by rotating the metering drum (2), the dose is ready to be inhaled from the dosing cup by the patient through the mouthpiece (20). As the patient inhales through the device, ambient air enters into the air inlet passage (6) through an inlet orifice (5). The inlet passage (6) is of constant cross-section and of essentially rectangular shape, as shown in FIGS. 2 to 4, so as to moderate the turbulence level before the flow reaches the dosing cup. Based on the minimum inlet dimension (21), the air inlet passage (6) cross section is defined such that the Reynolds Number (Re) for the flow at peak flow conditions is below 5000.

Figure 5:
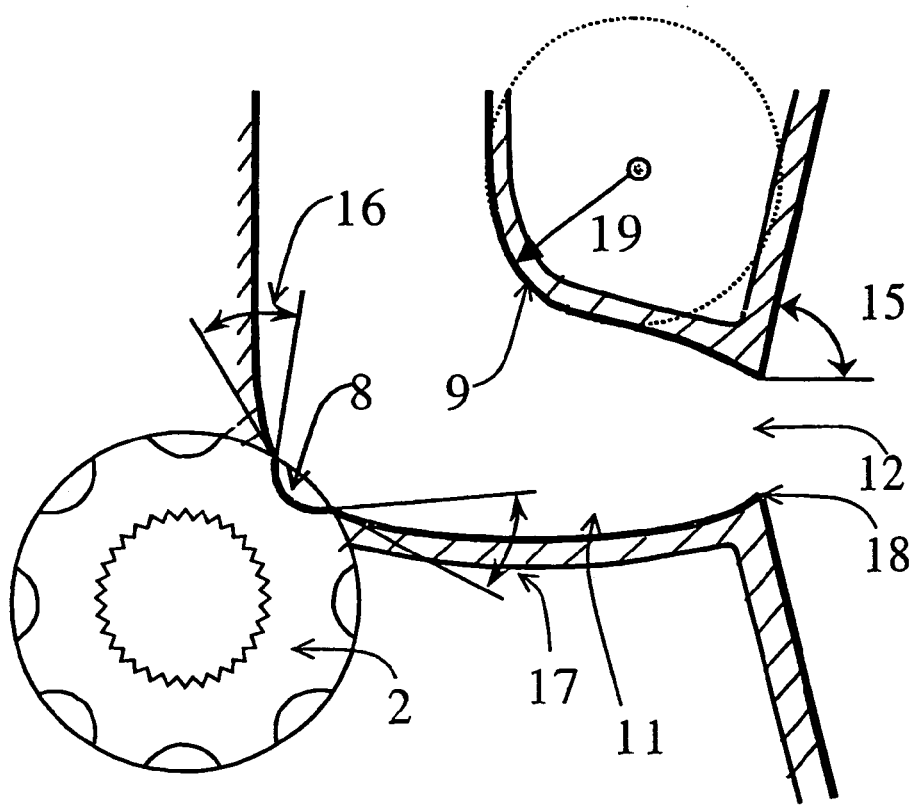
FIG. 5 shows a close up of a cross section of the transition passage and converging passage of the device of FIG. 1 along the vertical symmetry plane.

The air inlet passage (6) is followed by a transition passage, which in this embodiment is in the form of a turning passage (7). The turning passage (7) is shown in more detail in FIG. 5. The radius of curvature (19) of the inner wall (9) of the turning passage (7) is about one half of the shortest dimension (21) of the inlet passage (6) so as to prevent re-circulation in the region near the inner wall (9). The outer wall (10) of the turning passage (7) has a slot-like aperture, into which the periphery of the metering drum (2) is fitted such that a dosing cup (8) is smoothly integrated into the outer wall (10) of the interior of the turning passage (7). The cross-section of the dosing cup (8) is semicircular in shape. The angles 16 and 17 between the wall of the dosing cup (8) and the outer wall (10) of the turning passage (7), best seen in FIG. 5, are about 35 degrees. As shown in FIG. 4, which depicts the cross-sectional areas of the various passages of the device, the cross-sectional area of the turning passage (7) is essentially rectangular with slightly tapering bottom and becomes greater than the cross-sectional area of the inlet passage (6). This together with the turn has the effect of reducing the velocity of fluid in the dosing cup (8) so as to delay aerosolization until the flow is sufficiently developed. As shown in FIG. 4, the width of the dosing cup (8) is about equal to the width of the rectangular bottom of the turning passage (7).

The turning passage (7) is followed by the converging passage (11) smoothly connected thereto. As can be seen from FIGS. 3 and 4, the cross-section of the converging passage (11) is rectangular and evenly converging. Its end forms an oval formed throat (12) acting as a nozzle. As can be seen in FIG. 4, the cross-sectional area of the throat (12) is significantly smaller than the cross-sectional areas of the air inlet (6), turning (7) and converging passages (11). Thus the throat (12) controls the pressure drop across the entire device. The turning angle between the longitudinal axis of the air inlet passage (6) and the longitudinal axis of the converging passage (11) is approximately 90 degrees.

Figure 6:
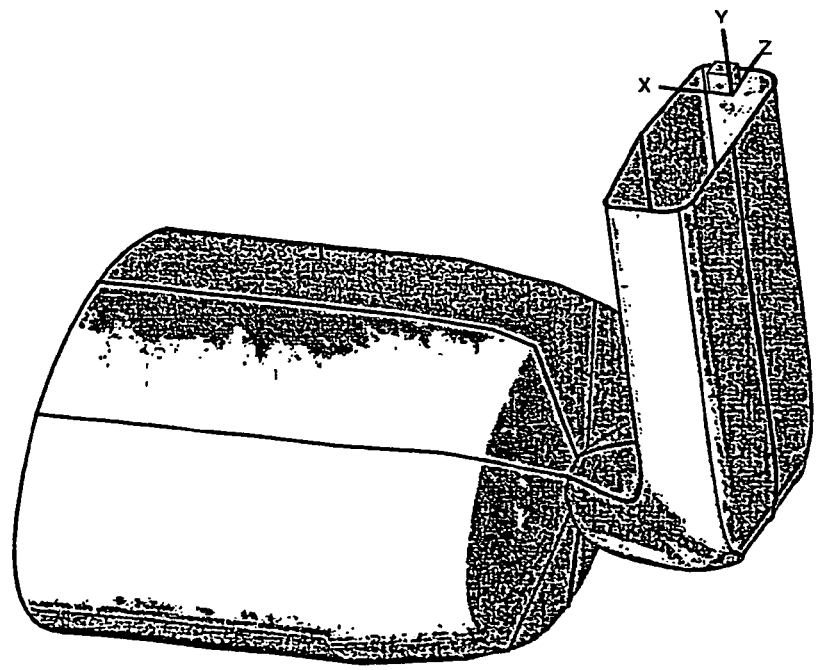
FIG. 6 is an isometric view of inner surface of a device according to the invention.

The throat (12) opens sharply to the diverging section having oval cross-section (13) at an angle (15) of about 87 degrees, as shown in FIGS. 1, 3 and 6. The diverging section (13) is followed by an intermediate section diverging with a relatively small angle and, finally, an outlet passage (14) having a constant oval formed cross-section and relatively large cross-sectional area. The end of the outlet passage (14) forms the mouthpiece (20) of the device. The radius of curvature of the throat corner (18) is small such that the flow readily detaches from the wall of the diverging section (13) and creates a free jet generating high levels of turbulence far from the damping effects of nearby walls. The length of the outlet passage (14) is selected such that a controlled free jet is formed before entering the mouth of the user. The distance between the throat (12) and the end of the outlet passage (14) is typically longer than the minimum dimension (24) of the outlet passage (14).

Figure 7:
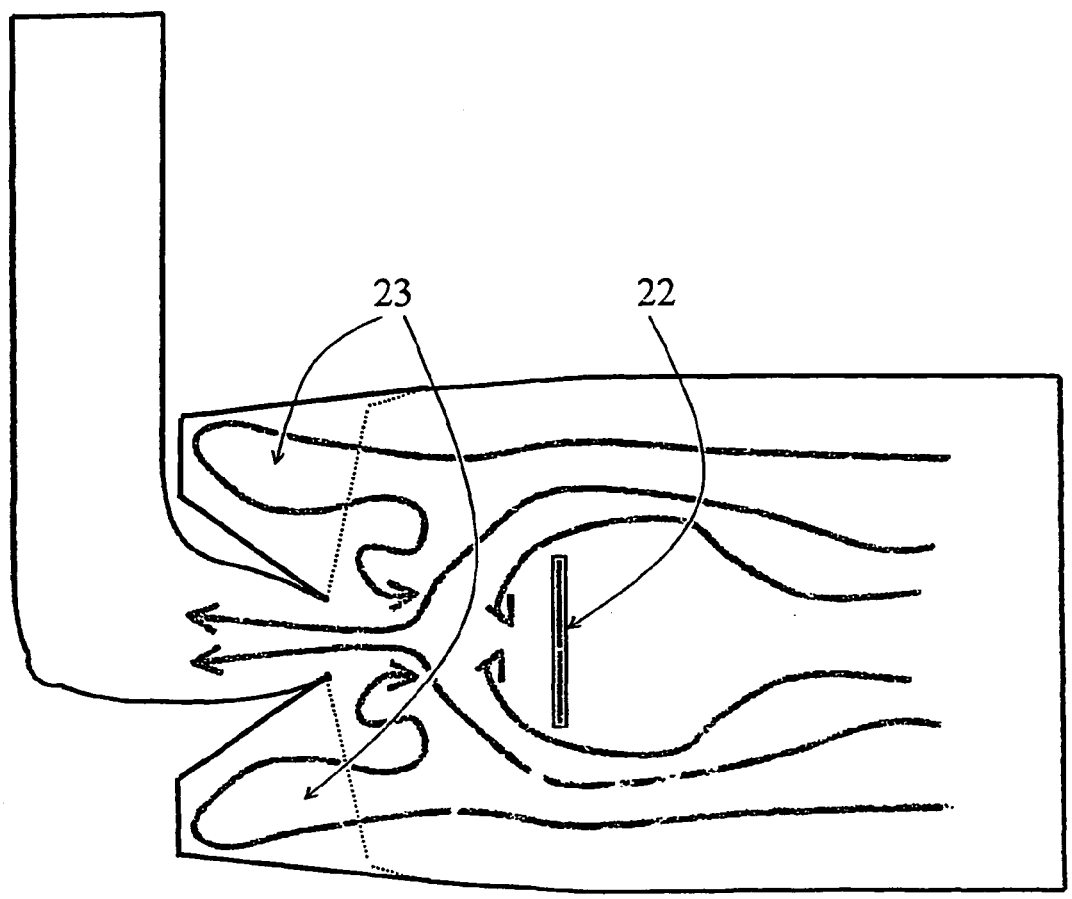
FIG. 7 is a schematic drawing showing an impactor plate and a dead end zone in a device according to the invention.

FIG. 7 shows schematically another embodiment of the invention comprising an impaction plate (22) mounted in the outlet passage (14). The impaction plate (22) is placed in the path of the free jet, but far enough downstream to allow some particle break-up due to turbulent shear. Large carrier particles are impacted on the plate to enhance deagglomeration. At the same time, the free jet is diminished before entering the mouth. Already deagglomerated drug particles, with low inertia, pass the plate (22) without impaction. The impaction plate (22) can be secured into the outlet passage (14) in number of ways, which are obvious to one skilled in the art.

The embodiment of FIG. 7 also incorporates a dead end zone (23) adapted to maximize flow disturbances and pressure drop and thereby reduce backflow when the user exhales into the device by misuse. The diverging angle (15) of the diverging section (13) is in such embodiment large, typically more than 120 degrees.

It is preferred that the critical regions of the device which determine pressure drop and turbulence levels will consist of single moulded pieces to maintain device-to-device consistency.

Figure 8:
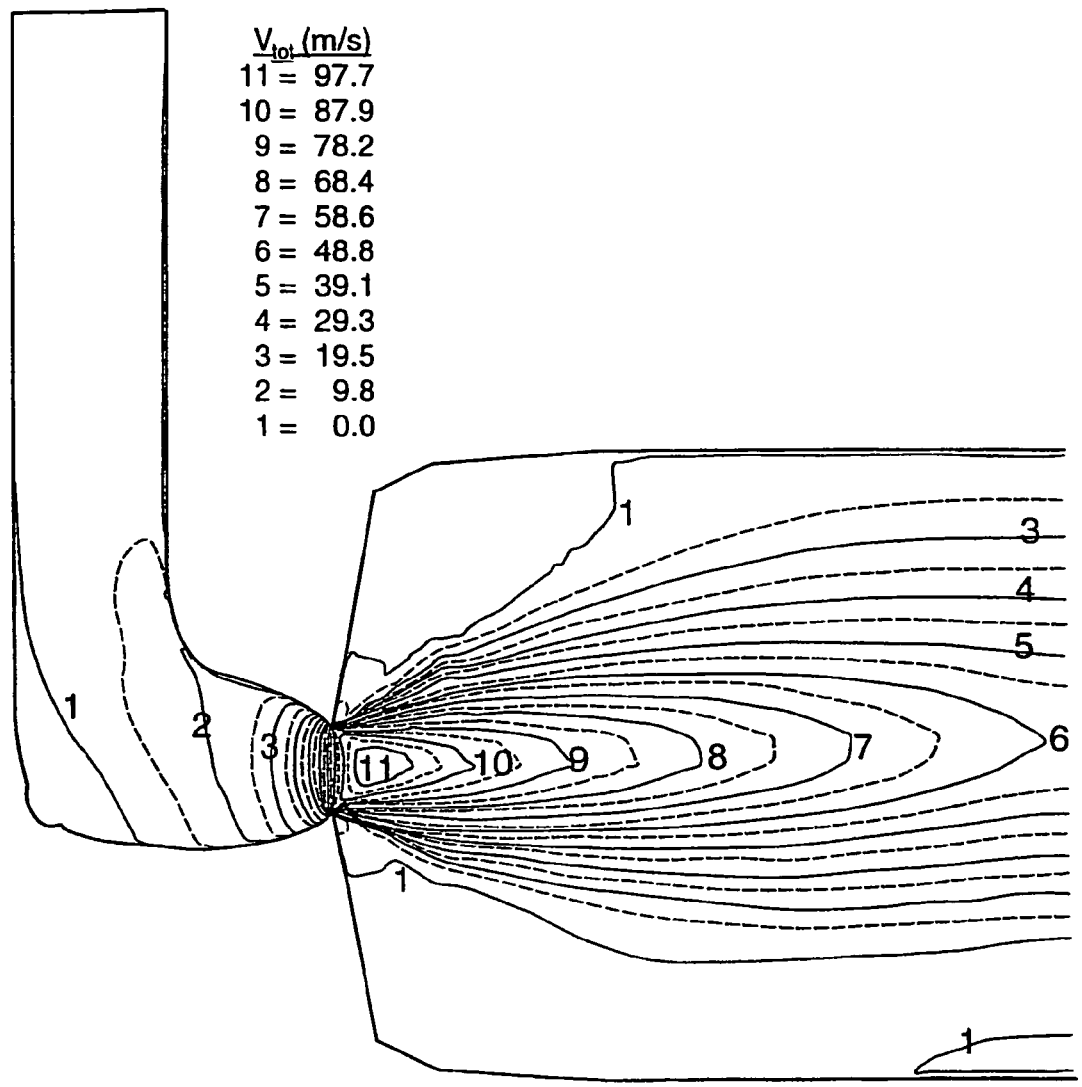
FIG. 8 shows contours of the total velocity of air in a device according to the invention.
Figure 9:
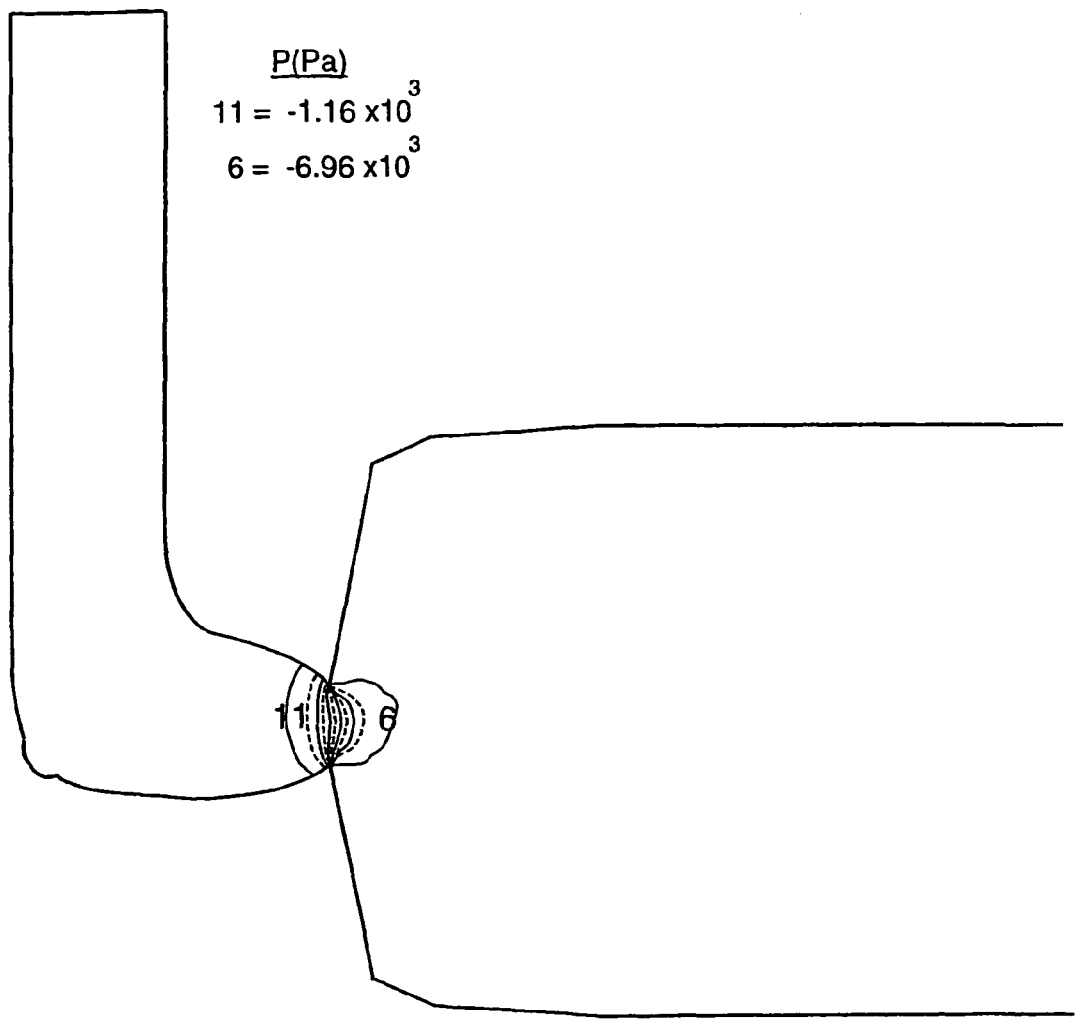
FIG. 9 shows contours of the static pressure of air in a device according to the invention.
Figure 10:
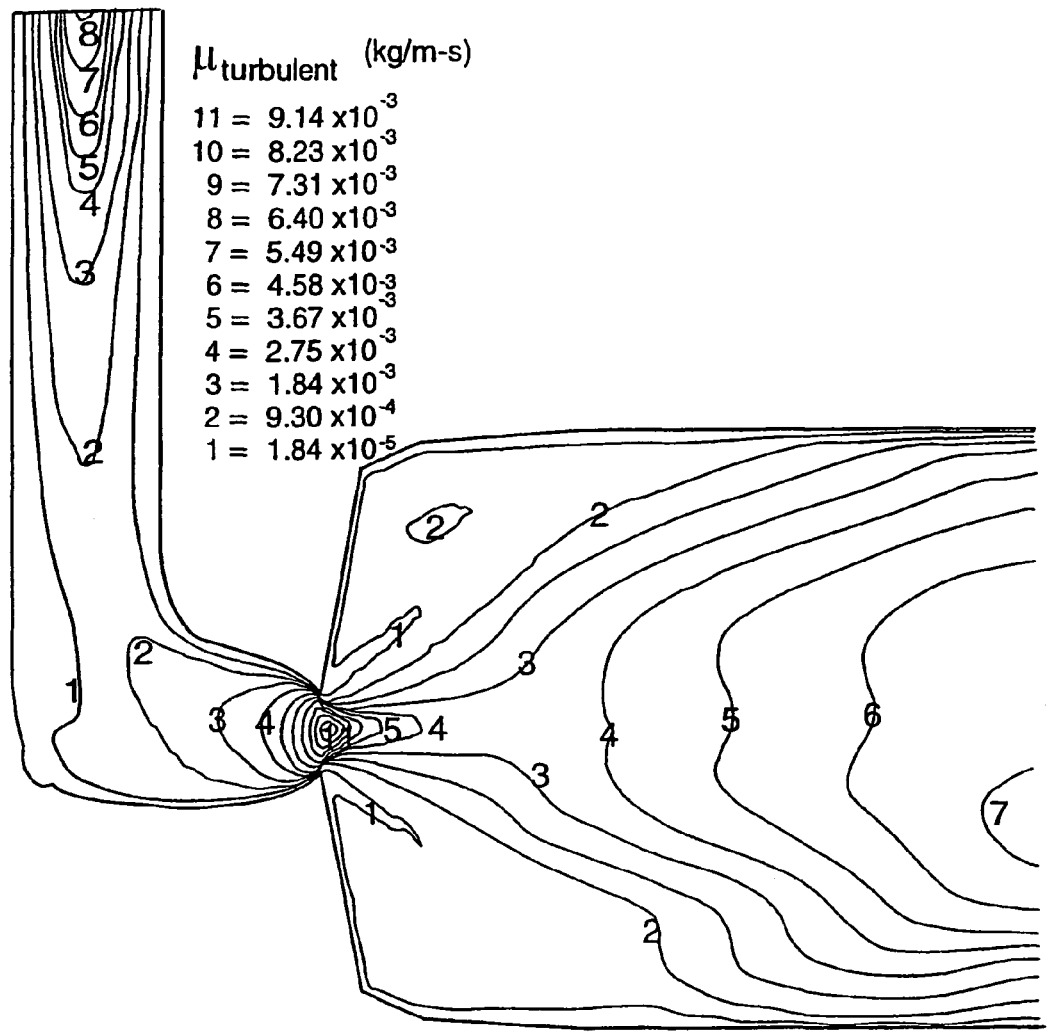
FIG. 10 shows contours of the turbulent viscosity $\mu$ of air in a device according to the invention.
Figure 11:
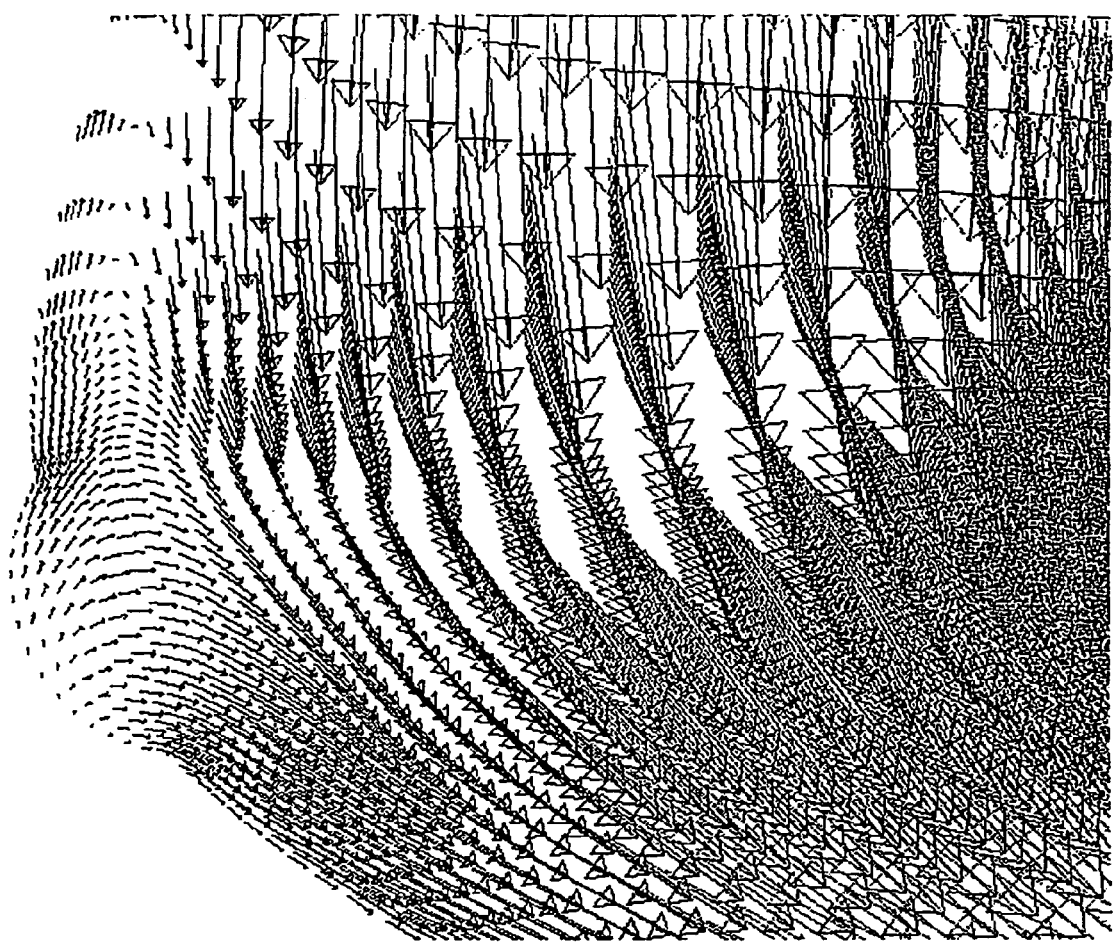
FIG. 11 shows velocity vectors in and around the dosing cup in a device according to the invention.

Calculations based on Computational Fluid Dynamics (CFD) were performed to characterize the fluid behavior of the device of the invention. FIGS. 8 to 10 show the calculated velocity, pressure and turbulent viscosity under 60 L/min steady slate conditions for the device of FIG. 1. It can be seen that the peak velocity and pressure drop occurs just downstream of the nozzle and within the jet region of the device. Peak turbulence occurs at the device throat and downstream in the mouth region. Pressure drop in this design is approximately 6.5 kPa. Maximum turbulence is in the near throat region with a turbulent viscosity of approximately $1 \times 10^{-2}$ kg/m/s. Calculations show that this level of turbulence is sufficient to break up the vast majority of aerosolized powders. Flow in the dosing cup is uniform and of low velocity relative to the peak velocity. FIG. 11 shows the flow in this region. There are no small-scale dead zones and the flow in the cup is on the order of 2.5 m/s at peak flow conditions. This is sufficient to aerosolize the vast majority of drug particles. The flow transient indicates that the flow always remains attached to the inside surface of the turn in the dosing chamber and that peak velocities always occur near the insides surface of the turn. Consequently, velocities in the dosing cup are always lower than at the peak of the inhalation cycle and aerosolization of particles is effectively delayed without the use of complex release mechanisms.

Figure 12:
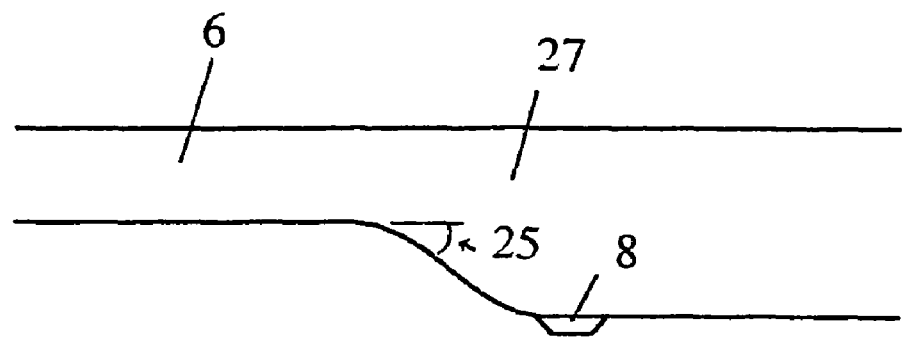
FIG. 12 is a schematic picture of one embodiment of the transition passage comprising an expansion.
Figure 14:
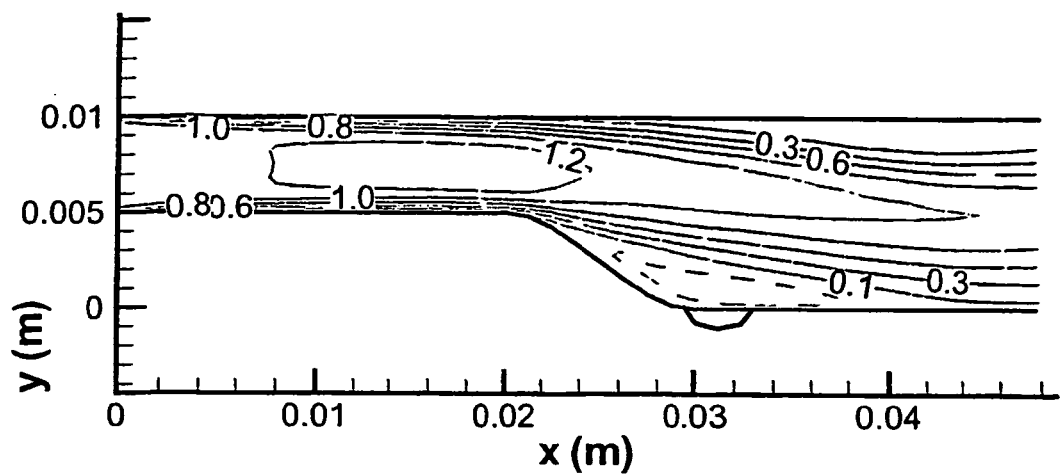
FIG. 14 shows axial velocity curves in the transition passage according to FIG. 12.

FIG. 12 shows another preferred embodiment of the transition passage. In this case the transition passage having rectangular cross-section runs essentially parallel to the air inlet passage (6), to which it is smoothly integrated. Instead of a turn, the transition passage comprises a rapid expansion (27) of rectangular cross-section in the direction of the bottom of the passage. The opening angle (25) of the expansion (27) is about 30 degrees and the maximum cross-sectional area about 2 times larger than that of the rectangular air inlet passage (6). The dosing cup (8) is disposed immediately downstream of the expansion (27). A flow calculation of this embodiment is shown in FIG. 14 the curves depicting axial air velocity values (n/s). It can be seen that a region of reduced air velocity is created immediately downstream of the expansion (27) and that the dosing cup (8) resides in the reduced air velocity region.

Figure 13:
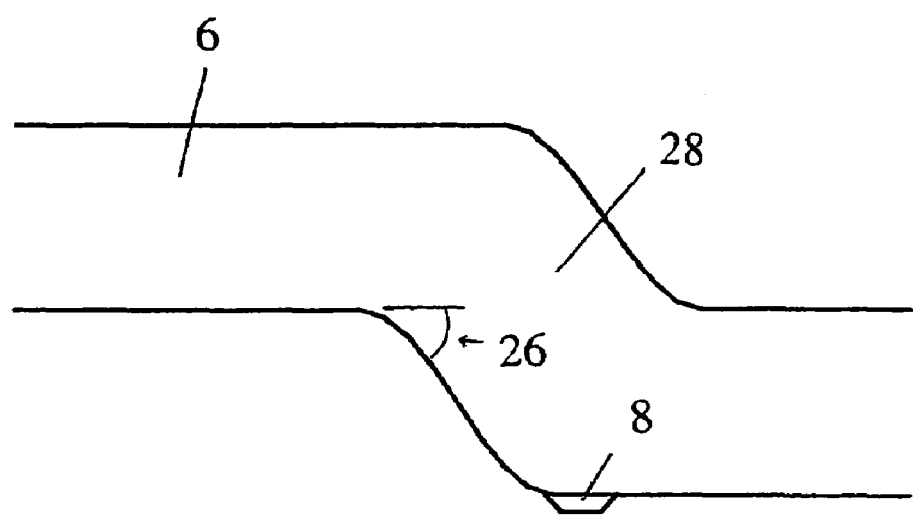
FIG. 13 is a schematic picture of one embodiment of the transition passage comprising a multiple turn.
Figure 15:
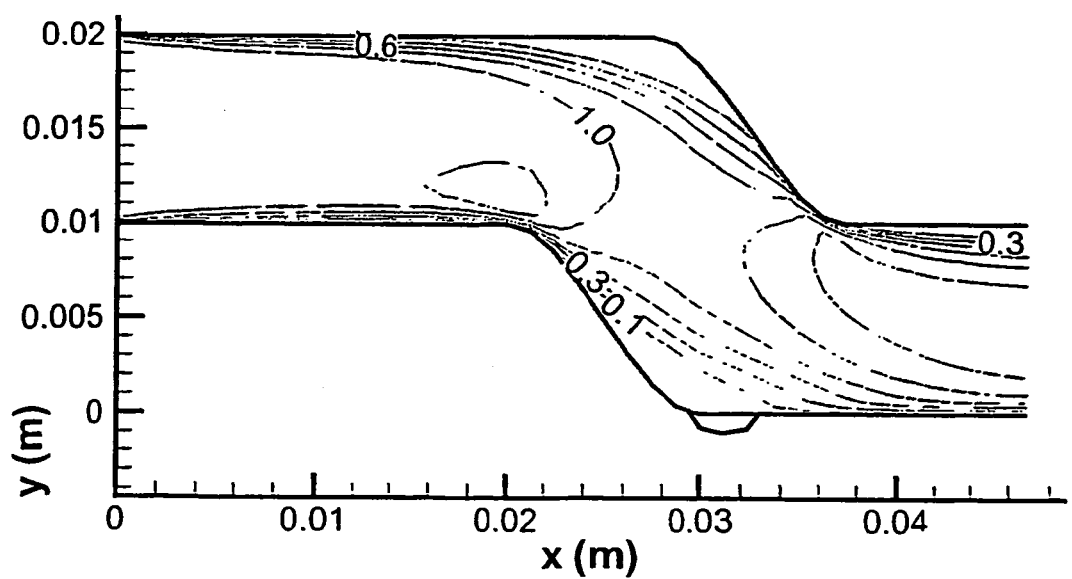
FIG. 15 shows axial velocity curves in the transition passage according to FIG. 13.

FIG. 13 shows still another preferred embodiment of the transition passage. In this case the transition passage has a constant rectangular cross-sectional area and comprises a multiple turn (28) in the form of two successive uniplanar turns with the turning angle (26) of about 45 degrees. The distance between the turns is approximately equal to the height of the rectangular transition passage. A flow calculation of this embodiment is shown in FIG. 15 the curves depicting axial air velocity values (m/s). It can be seen that a region of reduced air velocity is created immediately downstream of the multiple turn (28) and that the dosing cup (8) resides in the reduced air velocity region.

Modifications and variations can be made to the disclosed embodiments without departing from the subject of the invention as defined in the following claims. It is considered to be routine for one skilled in the art to make such modifications to the device of the invention.

What is claimed is:

1. A device for dispensing powdered medicament by inhalation, comprising
   an air inlet passage,
   a transition passage connected to the air inlet passage, said transition passage comprising a holding portion for a dose of powdered medicament and a means for creating a region of reduced air velocity,
   a converging passage connected to the transition passage, the converging passage comprising an end that forms a throat,
   a diverging section connected to the throat, and
   an air outlet passage connected to the diverging section,
   wherein the throat, the air inlet passage, the transition passage and the outlet passage each define a cross-sectional area that includes a minimum cross-sectional area,
   and wherein the cross-sectional area of the throat is smaller than the minimum cross-sectional area of the air inlet passage, the transition passage and the outlet passage,
   wherein a dose of powdered medicament can be aerosolized from the holding portion by way of an air stream produced by inhalation.

2. A device according to claim 1, wherein the cross-sectional area of the throat is less than 50% of the minimum cross-sectional area of the air inlet passage, the transition passage and the outlet passage.

3. A device according to claim 2, wherein the cross-sectional area of the throat is less than 35% of the minimum cross-sectional area of the air inlet passage, the transition passage and the outlet passage.

4. A device according to claim 1, wherein the cross-sectional area of the outlet passage is larger than the cross-sectional area of the air inlet passage.

5. A device according to claim 1, wherein the cross-sectional area of the outlet passage is larger than three times the cross-sectional area of the throat.

6. A device according to claim 5, wherein the cross-sectional area of the outlet passage is larger than twenty times the cross-sectional area of the throat.

7. A device according to claim 1, wherein the flow Reynolds Number of the air inlet passage is below 5000.

8. A device according to claim 7, wherein the flow Reynolds Number of the air inlet passage is below 4000.

9. A device according to claim 1, wherein the cross-sectional area of the air inlet passage is essentially constant.

10. A device according to claim 1, wherein the diverging section has a divergence angle greater than about 10 degrees.

11. A device according to claim 1, wherein the cross-section of the throat is oval in shape.

12. A device according to claim 1, wherein the length of the air inlet passage is greater than three times the shortest dimension of the air inlet passage.

13. A device according to claim 1, wherein the cross-section of the outlet passage is oval in shape.

14. A device according to claim 1, wherein the transition passage comprises a turn.

15. A device according to claim 14, wherein the transition passage forms a turn which is from about 10 to about 170 degrees.

16. A device according to claim 14, wherein the turn of the transition passage comprises an outer face, and wherein the shape of the holding portion for a dose of powdered medicament is such that it is smoothly integrated into the outer face of the turn of the transition passage.

17. A device according to claim 14, wherein the turn of the transition passage comprises an inner face, and wherein the radius of curvature of the inner face of the turn of the transition passage is greater than 20% of the shortest dimension of the air inlet passage.

18. A device according to claim 14, wherein the cross-sectional area of the transition passage is larger than that of the air inlet passage.

19. A device according to claim 14, wherein the transition passage forms a turn which is from about 45 to about 135 degrees.

20. A device according to claim 14, wherein the transition passage forms a turn which is about 90 degrees.

21. A device according to claim 14, wherein the turn of the transition passage comprises an inner face, and wherein the radius of curvature of the inner face of the turn of the transition passage is about 50% of the shortest dimension of the air inlet passage.

22. A device according to claim 1, wherein the transition passage comprises an expansion.

23. A device according to claim 1, wherein the transition passage comprises a multiple turn.

24. A device according to claim 1, wherein the air inlet passage is smoothly integrated with the transition passage.

25. A device according to claim 1, wherein the holding portion for a dose of powdered medicament is a dosing cup of a metering member adapted to meter a dose of powdered medicament from a medicament reservoir of the device.

26. A device according to claim 1, wherein the transition passage is smoothly integrated with the converging passage.

27. A device according to claim 1, wherein the diverging section forms a dead end zone to minimize backflow.

28. A device according to claim 1, comprising additionally an impactor plate positioned in the outlet passage.

29. A device according to claim 1, wherein the cross-section of the air inlet passage, the transition passage and/or the converging passage is essentially rectangular in shape.

30. A device for dispensing powdered medicament by inhalation, comprising
an air inlet passage,
a transition passage in the form of a turning passage connected to the air inlet passage, wherein the turning passage comprises an outer wall,
a holding portion for a dose of powdered medicament on the outer wall of the turn of the transition passage,
a converging passage connected to the transition passage, the converging passage comprising an end that forms a throat,
a diverging section connected to the throat, and
an air outlet passage connected to the diverging section,
wherein the throat, the air inlet passage, the transition passage and the outlet passage each define a cross-sectional area that includes a minimum cross-sectional area,
and wherein the cross-sectional area of the throat is smaller than the minimum cross-sectional area of the air inlet passage, the transition passage and the outlet passage,
wherein a dose of powdered medicament can be aerosolized from the holding portion by means of an air stream produced by inhalation.

* * * * *